US009235907B2

(12) United States Patent
Ramirez Giraldo et al.

(10) Patent No.: US 9,235,907 B2
(45) Date of Patent: Jan. 12, 2016

(54) SYSTEM AND METHOD FOR PARTIAL SCAN ARTIFACT REDUCTION IN MYOCARDIAL CT PERFUSION

(71) Applicants: Juan C. Ramirez Giraldo, Chapel Hill, NC (US); Cynthia H. McCollough, Byron, MN (US)

(72) Inventors: Juan C. Ramirez Giraldo, Chapel Hill, NC (US); Cynthia H. McCollough, Byron, MN (US)

( * ) Notice: Subject to any disclaimer, the term of this patent is extended or adjusted under 35 U.S.C. 154(b) by 327 days.

(21) Appl. No.: 13/804,796

(22) Filed: Mar. 14, 2013

(65) Prior Publication Data
US 2013/0251229 A1 Sep. 26, 2013

Related U.S. Application Data

(60) Provisional application No. 61/613,475, filed on Mar. 20, 2012, provisional application No. 61/625,415, filed on Apr. 17, 2012.

(51) Int. Cl.
*G06K 9/00* (2006.01)
*A61B 6/00* (2006.01)
*G06T 11/00* (2006.01)
*A61B 6/03* (2006.01)

(52) U.S. Cl.
CPC .............. *G06T 11/003* (2013.01); *A61B 6/032* (2013.01); *A61B 6/481* (2013.01); *A61B 6/486* (2013.01); *A61B 6/487* (2013.01); *A61B 6/503* (2013.01); *A61B 6/507* (2013.01); *A61B 6/5264* (2013.01); *A61B 6/541* (2013.01); *G06T 11/006* (2013.01); *G06T 2211/412* (2013.01); *G06T 2211/432* (2013.01); *G06T 2211/436* (2013.01)

(58) Field of Classification Search
None
See application file for complete search history.

(56) References Cited

U.S. PATENT DOCUMENTS

| 4,682,289 | A  | * | 7/1987 | Nishihara       | 378/14 |
| 5,740,224 | A  | * | 4/1998 | Muller et al.   | 378/11 |
| 6,385,286 | B1 | * | 5/2002 | Fitchard et al. | 378/65 |
| 6,400,789 | B1 | * | 6/2002 | Dafni           | 378/15 |
| 6,522,712 | B1 | * | 2/2003 | Yavuz et al.    | 378/4  |
| 6,934,353 | B2 | * | 8/2005 | Wang et al.     | 378/8  |
| 7,474,727 | B2 |   | 1/2009 | Vives et al.    |        |

(Continued)

FOREIGN PATENT DOCUMENTS

DE 102008055727 A1 5/2010

OTHER PUBLICATIONS

Heuscher, et al., Reduced Partial Volume Artifacts Using Spiral Computed Tomography and an Integrating Interpolator, Medical Physics, 1999, 26(2):276-286.

(Continued)

*Primary Examiner* — Wenpeng Chen
(74) *Attorney, Agent, or Firm* — Quarles & Brady, LLP

(57) ABSTRACT

A system and method is provided for reducing partial scan reconstruction artifacts in sinogram data acquired as a series of sets of partial-scan projection views, each set of projection views extending over an angular range of less than 360 degrees. A full-scan sinogram matrix for each of the sets of projection views in the series is created and each set of partial-scan projection views is stored in a respective full-scan sinogram matrix to create an array of full-scan matrices having respective empty spaces not filled by partial-scan projection view data stored therein. The empty spaces are filled in each of the full-scan sinogram matrices using the partial-scan projection view data stored therein and an image of the subject is reconstructed from the full-scan sinogram matrices having the empty spaces filled using the partial-scan projection view data stored therein.

21 Claims, 4 Drawing Sheets

(56) References Cited

U.S. PATENT DOCUMENTS

| | | | |
|---|---|---|---|
| 2003/0007593 A1* | 1/2003 | Heuscher et al. | 378/4 |
| 2004/0240604 A1* | 12/2004 | Wang et al. | 378/19 |
| 2005/0238135 A1* | 10/2005 | Younis et al. | 378/8 |
| 2005/0249432 A1* | 11/2005 | Zou et al. | 382/276 |
| 2005/0254621 A1* | 11/2005 | Kalender et al. | 378/46 |
| 2005/0265611 A1* | 12/2005 | Valadez | 382/236 |
| 2006/0198491 A1* | 9/2006 | Taguchi | 378/15 |
| 2006/0257010 A1* | 11/2006 | George et al. | 382/131 |
| 2007/0036418 A1* | 2/2007 | Pan et al. | 382/131 |
| 2007/0092055 A1* | 4/2007 | Vives et al. | 378/4 |
| 2007/0238956 A1* | 10/2007 | Haras et al. | 600/407 |
| 2008/0240335 A1* | 10/2008 | Manjeshwar et al. | 378/4 |
| 2009/0175562 A1* | 7/2009 | Pan et al. | 382/312 |
| 2009/0225934 A1* | 9/2009 | Hugg et al. | 378/20 |
| 2011/0044546 A1* | 2/2011 | Pan et al. | 382/195 |
| 2011/0103542 A1* | 5/2011 | Allmendinger et al. | 378/4 |
| 2011/0142315 A1* | 6/2011 | Hsieh et al. | 382/131 |
| 2011/0164799 A1* | 7/2011 | Miao et al. | 382/131 |
| 2011/0293155 A1* | 12/2011 | Nakanishi et al. | 382/131 |
| 2012/0136236 A1* | 5/2012 | Roberts | 600/411 |

OTHER PUBLICATIONS

Hsieh, et al., Fractional Scan Algorithms for Low-Dose Perfusion CT, Med. Phys., 2004, 31(5):1254-1257.

Meinel, et al., Reduction of Half-Scan Shading Artifact Based on Full-Scan Correction, Academic Radiology, 2006, 13(1):55-62.

Montes, et al., Analysis of Time Resolution in Dynamic Computed Tomography for Perfusion Studies, Nuclear Science Symposium Conference Record, 2004 IEEE, 7:4195-4199.

Montes, et al., A Temporal Interpolation Approach for Dynamic Reconstruction in Perfusion CT, Med. Phys., 2007, 34(7):3077-3092.

Primak, et al., A Technical Solution to Avoid Partial Scan Artifacts in Cardiac MDCT, Med. Phys., 2007, 34(12):4726-4737.

Stenner, et al., Partial Scan Artifact Reduction (PSAR) for the Assessment of Cardiac Perfusion in Dynamic Phase-Correlated CT, 2008 IEEE Nuclear Science Symposium Conference Record, pp. 5203-5209.

Stenner, et al., Partial Scan Artifact Reduction (PSAR) for the Assessment of Cardiac Perfusion in Dynamic Phase-Correlated CT, Med. Phys., 2009, 36(12):5683-5694.

Ramirez-Giraldo JC et al. A strategy to decrease partial scan reconstruction artifacts in myocardial perfusion CT: Phantom and in vivo evaluation. Medical Physics, 39(1), p. 214-223, 2012.

Primak AN. Medical Physics, 2008. A technical solution to avoid partial scan artifacts in cardiac MDCT. Medical Physics 34, p. 4726-4737, 2007.

Parker DL. Optimal short scan convolution reconstruction for fanbeam CT. Medical Physics 9(2): 254-7, 1982.

* cited by examiner

SYSTEM AND METHOD FOR PARTIAL SCAN ARTIFACT REDUCTION IN MYOCARDIAL CT PERFUSION

CROSS-REFERENCE TO RELATED APPLICATIONS

This application is based on, claims the benefit of, and incorporates herein by reference U.S. Provisional Patent Application Ser. No. 61/613,475, entitled, filed Mar. 20, 2012, and entitled "SYSTEM AND METHOD FOR PARTIAL SCAN ARTIFACT REDUCTION IN MYOCARDIAL CT PERFUSION" and also U.S. Provisional Patent Application Ser. No. 61/625,415, entitled, filed Apr. 17, 2012, and entitled "SYSTEM AND METHOD FOR PARTIAL SCAN ARTIFACT REDUCTION IN MYOCARDIAL CT PERFUSION"

STATEMENT REGARDING FEDERALLY SPONSORED RESEARCH

N/A

BACKGROUND OF THE INVENTION

The present invention relates generally to systems and methods for medical imaging and, particularly, to systems and methods for reducing partial scan reconstruction artifacts in computed tomography perfusion (CTP).

In a computed tomography ("CT") system, an x-ray source projects a fan-shaped or cone-shaped beam of x-rays that is collimated to lie within an x-y plane of a Cartesian coordinate system, termed the "imaging plane." The x-ray beam passes through the object being imaged, such as a patient, and impinges upon an array of radiation detectors. The intensity of the transmitted radiation is dependent upon the attenuation of the x-ray beam by the object, and each detector produces a separate electrical signal that is a measurement of the beam attenuation. The attenuation measurements from all of the detectors are acquired separately to produce a transmission profile at a particular view angle.

The source and detector array in a conventional CT system are rotated on a gantry within the imaging plane, and around the object so that the angle at which the x-ray beam intersects the object constantly changes. A group of x-ray attenuation measurements from the detector array at a given angle is referred to as a "view," and a "scan" of the object includes a set of views acquired at different angular orientations during one revolution of the x-ray source and detector, thereby giving rise to the term "view angle" as synonymous with "view" or "projection." In a two dimensional (2D) scan, data is processed to reconstruct an image that corresponds to a slice taken through the object. The prevailing method for reconstructing an image from 2D data is referred to in the art as the filtered backprojection technique. This process converts the attenuation measurements from a scan into integers called "CT numbers," or "Hounsfield units," which are used to control the brightness of a corresponding pixel on a display.

Myocardial CTP is important for evaluating the hemodynamic significance of coronary artery disease. The rapid developments in multidetector row CT, particularly its successful adoption for noninvasive cardiac imaging, raise the possibility of obtaining both anatomic and functional information from a single imaging modality. However, from a technical perspective, cardiac CT is challenging due to demands in temporal resolution. Strategies to improve temporal resolution include faster gantry rotation, dual- and multiple-source CT, and partial (or short) scan reconstructions. In myocardial CTP several consecutive partial scans are used to track the transient arrival and washout of intravascular contrast agent. Since myocardial CTP protocols are typically ECG-gated, according to a desired interval within the cardiac cycle (for example, diastolic phase), it is not possible to guarantee that the same angular data range (or view angles) is covered by each consecutive partial scan. As a consequence, artifactual CT number variations over time, called partial scan reconstruction artifacts (PSR artifacts or PSAs), arise due to minor deviations in the projection data due to physical effects, for example, such as scattering and beam hardening.

Solutions proposed to address PSAs include an invasive procedure in which the animal heart is paced in synchrony with the gantry rotation of a CT scanner, thus guaranteeing consistent angular ranges for each partial scan. This results in effective reduction or elimination of artifacts. However, the obvious disadvantage of such an approach is its invasiveness, which precludes its use in humans. More recently, two noninvasive methods to reduce PSAs have been proposed. The first uses a special data acquisition mode in which x-rays are applied to complete a full gantry rotation (full scan with 360 degrees of projection data). Then, based on the ECG signal, a specific phase of the cardiac cycle is selected and both a full and a partial scan are reconstructed. And by the use of convolution operations, a new image dataset containing the low spatial frequencies portion from a full scan (with no PSAs) and high spatial frequencies from a partial scan (free from motion artifact) is obtained. Such an approach is called the "targeted spatial frequency filter" (TSFF), and is currently implemented in the second generation dual source CT scanner (Somatom Definition Flash, Siemens Healthcare). A disadvantage of this approach is an increase in radiation dose (for example, 14%), and potential decreases in temporal resolution compared to a partial scan.

Another approach to PSAs was proposed by Stenner et al. (2010). In this approach, only partial scans from a myocardial CTP sequence are used. In this approach, the raw data of several consecutive partial scans are averaged such that a sinogram containing 360 degrees of projection data (a full scan) is created. This is referred to as the "artificial full scan sinogram." Then, a virtual partial scan sinogram is extracted from the artificial full scan sinogram, by selecting the projection data corresponding to an angular range identical to that of the acquired partial scan sinogram. Then, three image datasets are reconstructed from each corresponding sinogram. The last operation consists in subtracting the virtual scan image from the artificial scan image, leaving as a result the 'artifact' image. Then, the 'artifact image' is substrated from the original partial scan image resulting in a partial scan image free from artifact. Advantages of this method include that it is noninvasive, there is no added radiation dose, and temporal resolution is preserved. A disadvantage is that the method requires several image reconstruction steps (3 instead of 1); hence, computational requirements are increased at least threefold. Another disadvantage is that, in practice, the superposition operations are potentially error prone because of mismatches generated by motion artifacts due to the rapid heart motion, that is, when applying this technique in vivo.

Therefore, it would be desirable to have a system and method for the reduction or control of PSAs in CTP that is substantially non-invasive, that does not increase radiation dose, that preserves temporal resolution, and that is robust to motion artifacts. Additionally, it would be desirable to have a system and method for PSAs reduction that can be readily applied to existing myocardial CTP protocols available in commercial CT scanners.

SUMMARY OF THE INVENTION

The present invention overcomes the aforementioned drawback by providing a system and method for processing and reconstructing partial-scan data acquired by a CT system without the need to use specialized hardware, introduce additional dose to the patient, or endure burdensome computations. Rather, the present disclosure provides a system and method for transforming partial-scan sinogram data into full-scan sinogram data and reconstructing images form the full-scan sinogram data, without the drawbacks of traditional methods for overcoming PSAs described above.

In accordance with one aspect of the disclosure, a method for producing images of a subject acquired during subject motion using a medical imaging system and partial scan trajectories is provided. The method includes acquiring sinogram data of a subject formed as a series of sets of partial-scan projection views, each set of projection views extending over an angular range of less than 360 degrees from an initial view angle to a end view angle. The method also includes creating a full-scan sinogram matrix for each of the sets of projection views in the series and storing each set of partial-scan projection views in a respective full-scan sinogram matrix to create an array of full-scan matrices having respective empty spaces not filled by partial-scan projection view data stored therein. The method further includes filling the empty spaces in each of the full-scan sinogram matrices using the partial-scan projection view data stored therein and reconstructing an image of the subject from the full-scan sinogram matrices having the empty spaces filled using the partial-scan projection view data stored therein.

In accordance with another aspect of the disclosure, a computed tomography (CT) imaging system is disclosed that includes an x-ray source configured to emit x-rays toward an object to be imaged, a detector configured to receive x-rays that are attenuated by the object, and a data acquisition system (DAS) connected to the detector to receive an indication of received x-rays. The system also includes a computer system coupled to the x-ray source and DAS and programmed to control the x-ray source, detector, and DAS to acquire sinogram data of the object as a series of sets of partial-scan projection views, each set of projection views extending over an angular range of less than 360 degrees. The computer system is also programmed to create a full-scan sinogram matrix for each of the sets of projection views in the series and store each set of partial-scan projection views in a respective full-scan sinogram matrix to create an array of full-scan matrices having respective empty spaces not filled by partial-scan projection view data stored therein. The computer is further programmed to fill the empty spaces in each of the full-scan sinogram matrices using the partial-scan projection view data stored therein and reconstruct an image of the subject from the full-scan sinogram matrices having the empty spaces filled using the partial-scan projection view data stored therein.

In accordance with yet another aspect of the disclosure, a method for reducing partial scan reconstruction artifacts in computed tomography images acquired during subject motion using partial scan trajectories is provided. The method includes obtaining at least one set of medical imaging projection data from a subject undergoing motion using partial computed tomography scans having an associated angular range and storing the at least one set of medical imaging projection data in a matrix arranged according to view angle. The method also includes estimating medical imaging projection data in view angles outside the angular range covered by each partial computed tomography scan using at least one of a weighting and an interpolation based on the medical imaging projection data from neighboring partial computed tomography scans.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1A:
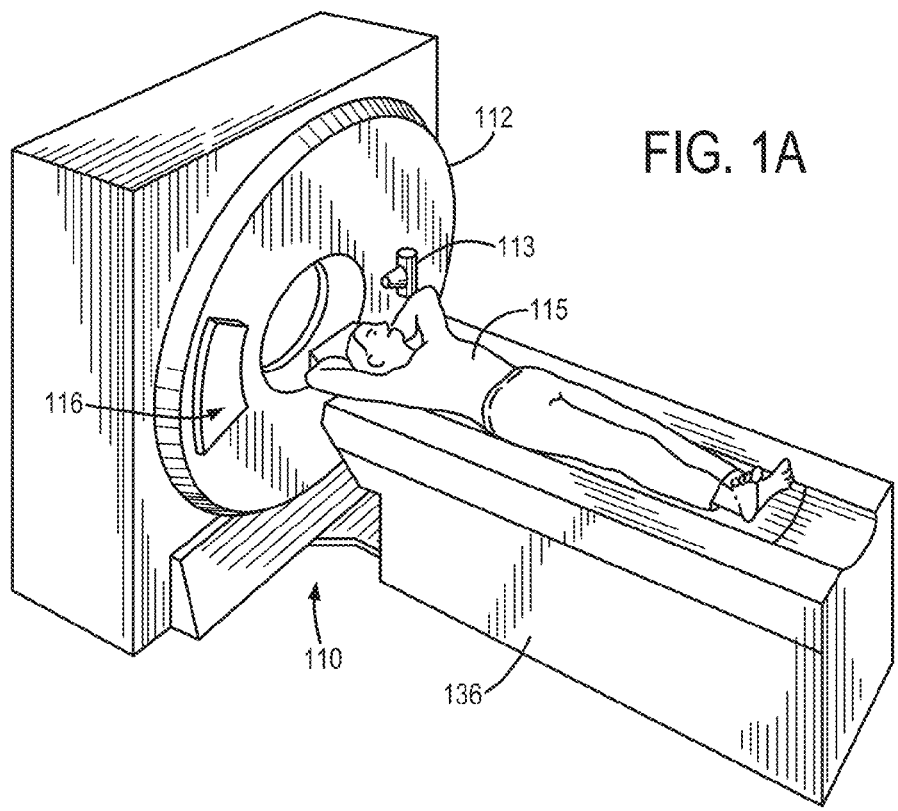
FIG. 1A is a pictorial view of an x-ray computed tomography (CT) imaging system for use with the present disclosure.
Figure 1B:
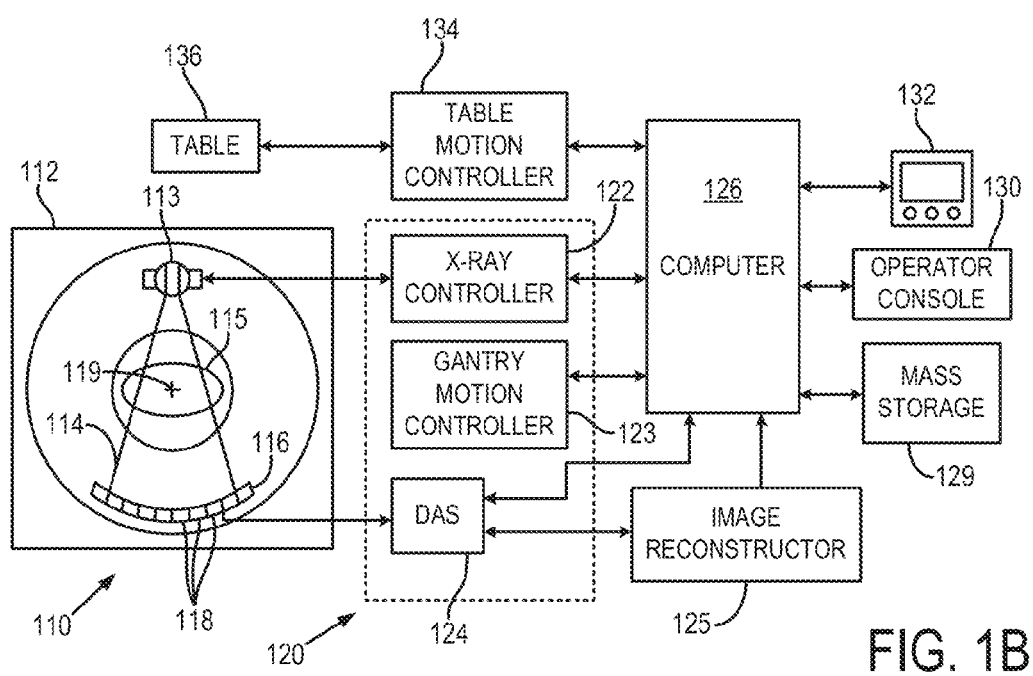
FIG. 1B is a block diagram of the CT imaging system of FIG. 1A.

With initial reference to FIGS. 1A and 1B, an x-ray computed tomography ("CT") imaging system 110 includes a gantry 112 representative of a "third generation" CT scanner. Gantry 112 has an x-ray source 113 that projects a fan-beam, or cone-beam, of x-rays 114 toward a detector array 116 on the opposite side of the gantry. The detector array 116 is formed by a number of detector elements 118 which together sense the projected x-rays that pass through a medical patient 115. Each detector element 118 produces an electrical signal that represents the intensity of an impinging x-ray beam and hence the attenuation of the beam as it passes through the patient. During a scan to acquire x-ray projection data, the gantry 112 and the components mounted thereon rotate about a center of rotation 119 located within the patient 115.

The rotation of the gantry and the operation of the x-ray source 113 are governed by a control mechanism 120 of the CT system. The control mechanism 120 includes an x-ray controller 122 that provides power and timing signals to the x-ray source 113 and a gantry motor controller 123 that controls the rotational speed and position of the gantry 112. A data acquisition system ("DAS") 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 which stores the image in a mass storage device 128.

The computer 126 also receives commands and scanning parameters from an operator via console 130 that has a keyboard. An associated display 132 allows the operator to observe the reconstructed image and other data from the computer 126. The operator supplied commands and parameters are used by the computer 126 to provide control signals and information to the DAS 124, the x-ray controller 122 and the gantry motor controller 123. In addition, computer 126 operates a table motor controller 134 which controls a motorized table 136 to position the patient 115 in the gantry 112.

Figure 2:
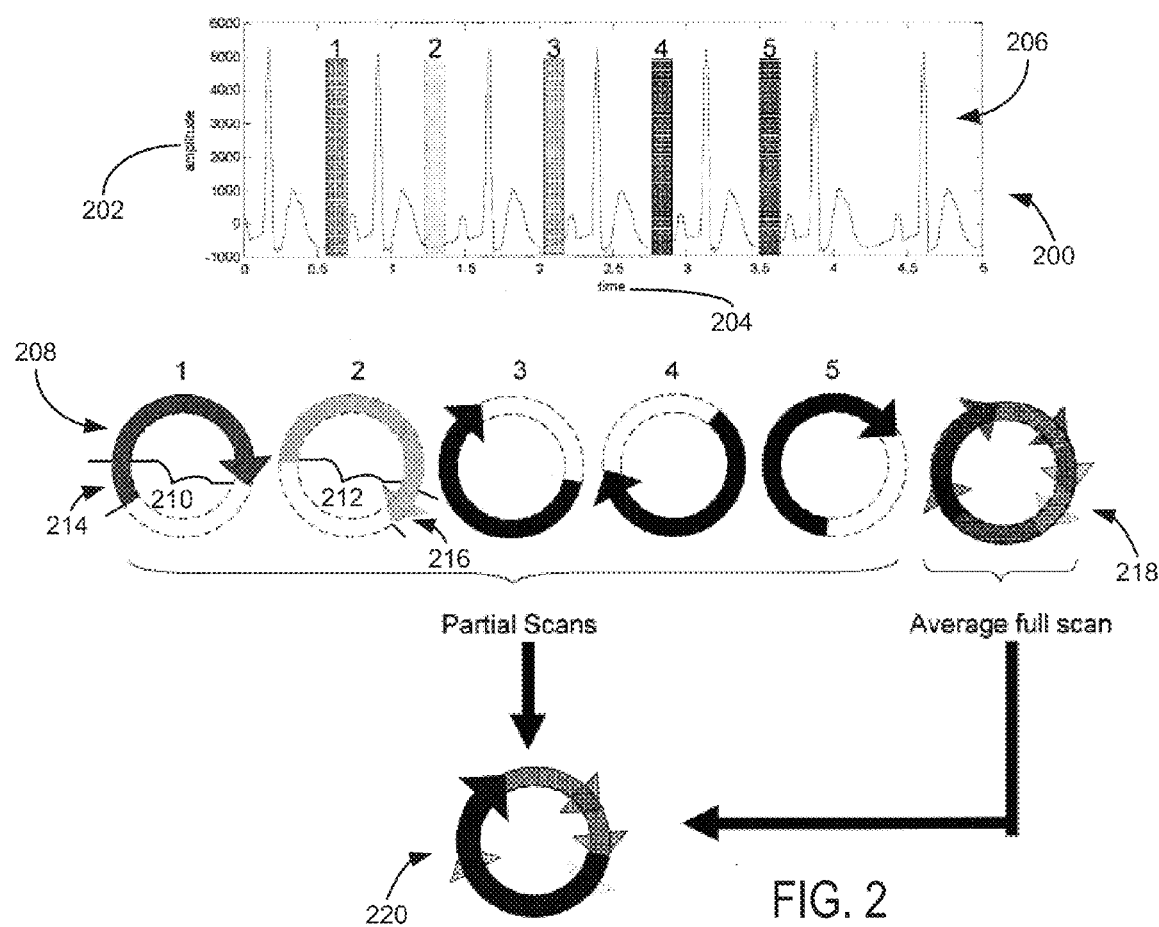
FIG. 2 is a diagram of partial CT image scans combined according to methods of the present disclosure.

Referring to FIG. 2, in accordance with the present disclosure, a myocardial CT perfusion (MYOCARDIAL CTP) scan or other CT scan including interventional CT and fluoroscopic CT can be divided into several consecutive partial scans that can be used to track the transient arrival and washout of intravascular contrast agent. Specifically, as illustrated in FIG. 2, a graph 200 of amplitude 202 versus time 204 during an acquisition of CT imaging data from a subject undergoing motion, such as cardiac motion, provides phase information 206. A series of partial scans 208 may be used to acquire image data in view angle ranges of, for example, 180 degrees, 180+alpha degrees, and/or 180−alpha degrees; using either single, dual, or multiple x-ray source approach.

In the illustrated non-limiting example, five partial scans are used to acquire the desired medical imaging data. The five partial scans in the example are number one (1) through five (5) and are acquired such that adjacent partial scans have partially overlapping scan regions 210, 212 but also non-overlapping scan regions 214, 216. Accordingly, when combined, an average full set of imaging data 218 is available. The partial scans 208 can improve temporal resolution, but partial scan reconstruction artifacts (PSAs) are observed due to different angular ranges of projections used. In accordance with the present disclosure, a method is provided that does not need to create an artificial full scan or a virtual scan to subtract or add either one to the original measured data. Rather, as will be described, PSR artifact reduction can be achieved by filling the missing data of a partial scan such that a full scan, free from artifact, can be reconstructed. To estimate the remaining 180+/−alpha projection information to complete a full scan, several phase-correlated time neighbor partial scans can be weighted to create a weighted average of temporal neighbors data set 220.

In accordance with the present disclosure, a method is provided for reducing PSA by filling missing data of a partial scan such that a full scan, free or appreciably free from artifact, can be reconstructed. More specifically, some embodiments of the present disclosure provide an algorithm to estimate the missing data of partial scans so that full scans in the projection space may be created with minimal or zero PSA.

In some methods of the present disclosure, data associated with each partial scan 208 is stored in a matrix called a sinogram that contains x-ray projection values (line integrals) at different view angles and detectors. For example, in a Somatom Definition CT Scanner (Siemens Healthcare, Forchheim, Germany), there are 1152 view angles and 672 detectors. However, as described above, the partial scan projection data collected may only cover an angular range of 180+/−alpha degrees, instead of a full 360 degrees. As a result, projection data may be missing for one or more view angles such that the average full scan 218 is not available.

Figure 3:
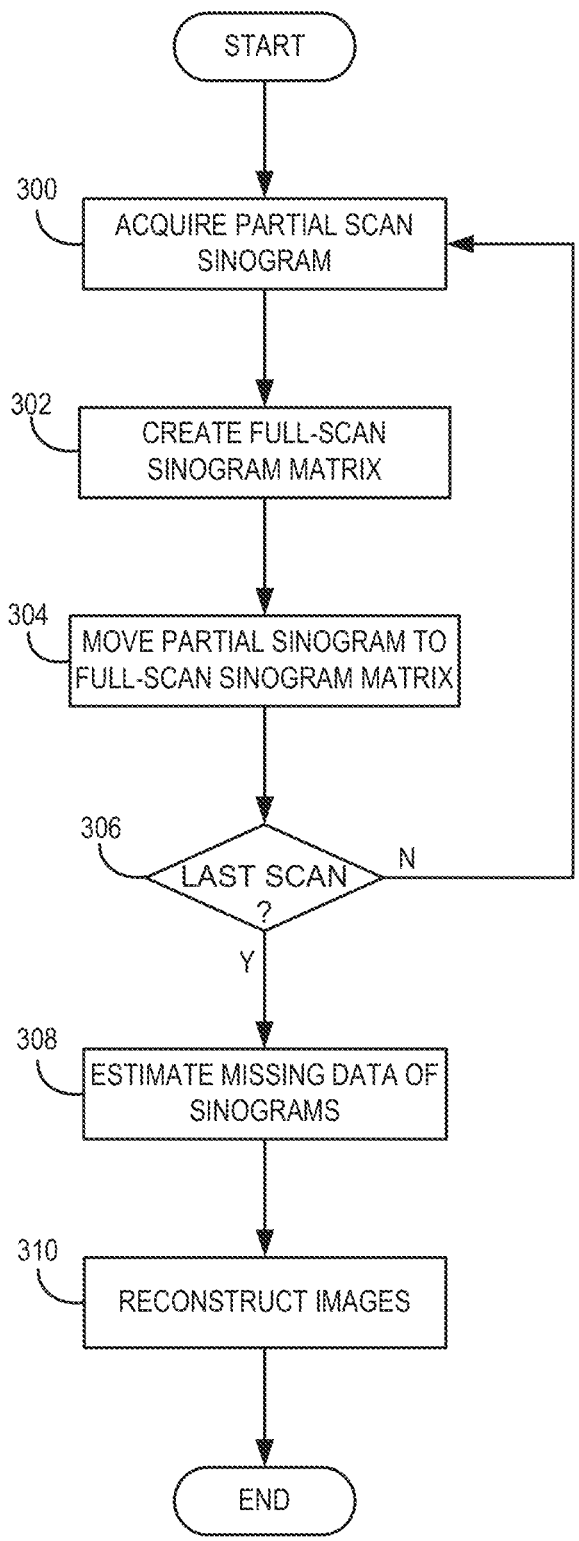
FIGS. 3 is a flow chart setting forth steps of an exemplary process in accordance with the present disclosure.
Figure 4:
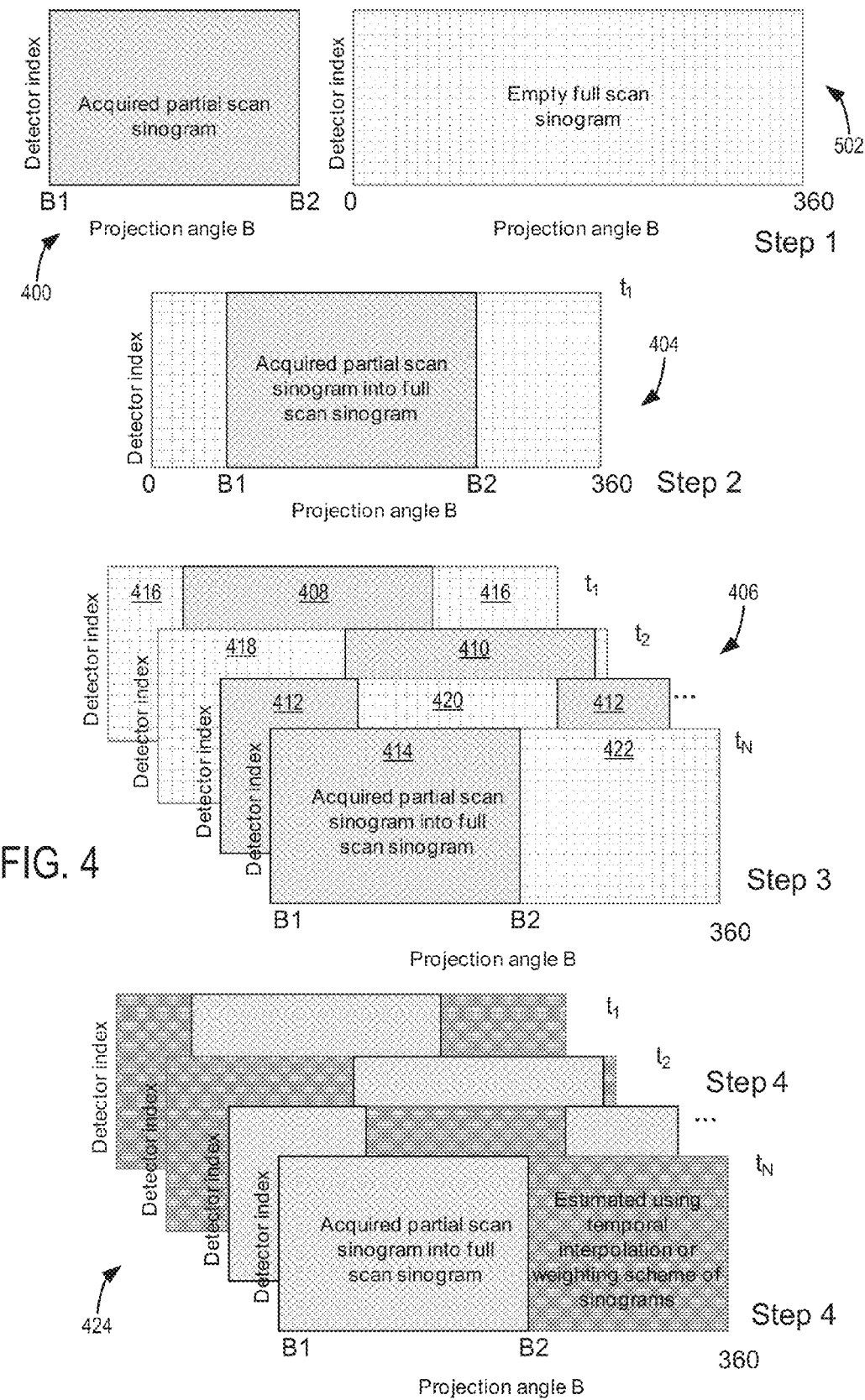
FIG. 4 is a schematic illustration of a process in accordance with the present disclosure.

Referring to FIGS. 3 and 4, a process for performing a CTP scan, while controlling PSAs will be described. At process block 300 partial scan sinograms expanding 180+alpha angular range are obtained. "Acquiring" or "obtaining" the sinogram data may include performing a scan of a subject using an imaging system such as described above or may include accessing previously-acquired data. Referring to FIG. 4, the acquision of one partial scan is illustrated at 400. In this example, data is obtained for each detector element (e.g. 672 detectors) at an initial angle B1 through an end angle B2, where B2−B1=180+alpha. At process block 302 of FIG. 3, an empty full-scan sinogram matrix 402 of FIG. 4, is created expanding from 0 to 360 degrees and across all detector elements, in the above example, spanning 672 detectors.

At process block 304, a partial scan sinogram at time $t_i$, with i=1 to N, is moved to a corresponding full-scan sinogram matrix expanding from 0 to 360 degrees. The full scan sinogram matrix is equal to the partial scan sinogram matrix from angular projection data corresponding to angles B1 to B2, and its empty otherwise. This is graphically illustrated in FIG. 4 at 404.

At decision block 306, a check is made to determine if all scans have been acquired. If not, the above-described steps are repeated. Thus, the above-described process is repeated for all acquired partial scan sinograms, such as illustrated in FIG. 4 at 406. As illustrated in FIG. 4, the partial scan sinogram fills only part of the full-scan sinogram matrix and, for each set of partial scan sinogram data extending over a set of view angles 408-414, is correspondingly aligned in the full scan sinogram matrix 416-422.

The resulting array of matrices has three dimensions, which are view angle, detector index, and time. Following thereafter, at process block 308, an interpolation or weighting scheme is applied in the temporal dimension, such that the missing data of the sinograms can be estimated. As illustrated in FIG. 4 at 424, the full-scan sinogram matrix is filled to include data estimated using temporal interpolation or weighting scheme of sinograms. Appropriate interpolation schemes may include but are not limited to linear or cubic splines. Appropriate weighting schemes can be used to average neighboring partial scans by considering both the distance in time (e.g. weighting higher the contributions from partial scans which are closer in time relative to partial scans farther in time), and/or intensity differences (e.g higher weights if attenuation value differences through time are small, and lower weight for the averaging process if difference through time are large). Typical weighting schemes to use can include but are not limited to exponential or linear weights.

As indicated at process block 310 of FIG. 3, the next step includes image reconstruction. Image reconstruction can be performed using methods such as the filtered backprojection or iterative reconstruction. It is contemplated that only the set of estimated full scan sinograms may be used for reconstruction. That is, the estimated/interpolated/weighted datasets that contained the originally-acquired sinogram and were completed by interpolation or weighting scheme can be used for reconstruction. Accordingly, an image of the subject acquired while undergoing motion can be reconstructed using the estimated medical imaging data and the imaging data from the partial scans that does not suffer from PSAs.

The above method makes uses of several consecutive partial scans such as that described by Stenner. However, only one set of sinograms (instead of 3) needs to be reconstructed. The method can employ a temporal interpolation of the sinograms, but it also can use a weighting scheme. It is targeted to time-series of consecutive partial CT scans such as the ones required in CTP applications to reduce PSAs. Further, because each reconstruction uses a larger number of projections (the estimated ones), the image noise (standard deviation of CT numbers) of reconstructed images is decreased; hence providing higher image quality or providing the possibility to reduce radiation dose. Furthermore, because only partial scans are used, motion artifacts are reduced when compared to full scan data acquisitions.

The methods of the present disclosure do not require further components or systems in addition to currently available CT scanners. For example, in some embodiments, storage of the projection data may occur in the above-described DAS 124 or another component of the control mechanism 120. In addition, one or more algorithms used to estimate missing sonogram data according to the method described above may be executed by the image reconstructor 125 and/or the computer 126. As a result, the methods of the present invention can be integrated into current myocardial CTP protocols available in CT scanners.

In testing, the above-described sinogram interpolation method of the present disclosure was able to consistently decrease CT number variations of partial scans to less than 20 percent in a stationary phantom. High temporal resolution was maintained because only partial scans contribute to the final data. Since more photons are used per scan, an extra benefit of the present method is that it can reduce noise by approximately 30 percent.

The systems and methods of the present disclosure are less complex than previous solutions for reducing PSA because they do not require additional x-ray exposures, as in the TSFF method, or the use of an artificial full scans or a virtual scan in addition to the original measured data, as in the Stenner method. In general, the system and methods of the present disclosure may have one or more of the following advantages over previous potential solutions. The methods reduce temporal CT number variations because full scans are estimated. Noise is reduced because more photons are used. Clinicians are provided with greater flexibility, for example, allowing only high temporal resolution contributions to be used for reconstruction. The methods maintain high fidelity in the time-attenuation-curves because the acquired data spanning a partial scan is preserved and only the missing projection data to complete a full scan is estimated with a proper interpolation or weighting method. The process is not computationally burdensome as the mathematics can rely on simple functions, such as exponential and linear functions, or spline interpolation, for the estimation of missing angular projections. The processes are independent of reconstruction parameters employed (e.g., filtered backprojection kernel or iterative reconstruction algorithm) because they are applied in the raw projection data domain. Advantageously, additional scans and radiation dosage are unnecessary because no prior information is needed. The process is compatible with myocardial CTP data acquired with either single or dual-source CT, with the later providing an advantage of faster scanning and, hence, better temporal resolution. Further, the methods disclosed can further increase temporal resolution with multi-segmented contributions lower than 180+alpha.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing images of a subject acquired during subject motion using a medical imaging system and partial scan trajectories, the method comprising the steps of:
   a) acquiring sinogram data of a subject formed as a series of sets of partial-scan projection views, each set of projection views extending over an angular range of less than 360 degrees from an initial view angle to an end view angle and differing angular ranges between sets in the series of sets of partial scan projection views;
   b) creating a full-scan sinogram matrix for each of the sets of projection views in the series;
   c) storing each set of partial-scan projection views in a respective full-scan sinogram matrix to create an array of full-scan matrices having respective empty spaces not filled by partial-scan projection view data stored therein;
   d) filling the empty spaces in each of the full-scan sinogram matrices using the partial-scan projection view data stored therein; and
   e) reconstructing an image of the subject from the full-scan sinogram matrices having the empty spaces filled using the partial-scan projection view data stored therein.

2. The method of claim 1 wherein the full-scan sinogram matrices have dimensions of at least two of view angle, detector index, and time.

3. The method of claim 2 wherein step d) includes applying at least one of an interpolation scheme and a weighting scheme in a temporal dimension to fill the empty spaces.

4. The method of claim 3 wherein weighting scheme uses one of exponential weights and linear weights.

5. The method of claim 3 wherein the interpolation scheme uses one of linear interpolation and cubic splines.

6. The method of claim 1 wherein step d) includes filling only a portion of the empty spaces.

7. The method of claim 1 wherein the medical imaging system includes a computed tomography (CT) system and the subject motion is cardiac motion.

8. The method of claim 7 wherein the set of partial-scan projection views tracks a transient arrival and washout of an intravascular contrast agent within the subject.

9. The method of claim 1 wherein the initial view angle and the end view angle of adjacent sets of partial-scan projection views in the series of sets of partial-scan projection views are offset by a predetermined angle.

10. The method of claim 9 wherein the predetermined angle is selected to create projection views adjacent sets of partial-scan projection views in the series of sets of partial-scan projection views that are both overlapping and non-overlapping.

11. A computed tomography (CT) imaging system comprising:
    an x-ray source configured to emit x-rays toward an object to be imaged;
    a detector configured to receive x-rays that are attenuated by the object;
    a data acquisition system (DAS) connected to the detector to receive an indication of the received x-rays;
    a computer system coupled to the x-ray source and DAS and programmed to:
       control the x-ray source, detector, and DAS to acquire sinogram data of the object as a series of sets of partial-scan projection views, each set of projection views extending over an angular range of less than 360 degrees to create partially overlapping scan regions and non-overlapping scan regions;
       create a full-scan sinogram matrix for each of the sets of the projection views in the series;
       store each set of partial-scan the projection views in a respective full-scan sinogram matrix to create an array of full-scan matrices having respective empty spaces not filled by partial-scan projection view data stored therein;
       fill the empty spaces in each of the full-scan sinogram matrices using the partial-scan projection view data stored therein; and
       reconstruct an image of the subject from the full-scan sinogram matrices having the empty spaces filled using the partial-scan projection view data stored therein.

12. The system of claim 11 wherein the full-scan sinogram matrices have dimensions of at least two of view angle, detector index, and time.

13. The system of claim 12 wherein the computer system is further configured to apply at least one of an interpolation scheme and a weighting scheme in a temporal dimension to fill the empty spaces.

14. The system of claim 13 wherein the computer system is further configured to us a weighting scheme including one of exponential weights and linear weights.

15. The system of claim 13 wherein the computer system is further configured to uses one of linear interpolation and cubic splines.

16. The system of claim 11 wherein the computer system is further configured to fill only a portion of the empty spaces.

17. The system of claim 11 wherein the series of sets of partial scan projection views includes sinogram data acquired from differing angular ranges of projections between sets of partial scan projection view.

18. A method for reducing partial scan reconstruction artifacts in computed tomography images acquired during subject motion using partial scan trajectories, the method comprising:
   obtaining at least two sets of medical imaging projection data from a subject undergoing motion using partial computed tomography scans having an associated and differing angular range;
   storing the at least two sets of medical imaging projection data in a matrix arranged according to view angle; and
   estimating medical imaging projection data in view angles outside the angular range covered by each partial computed tomography scan using at least one of a weighting and an interpolation based on the medical imaging projection data from neighboring partial computed tomography scans.

19. The method of claim 18 wherein the medical imaging projection data at neighboring partial computed tomography scans are weighted by one of exponential weights and linear weights.

20. The method of claim 18 further comprising storing the estimated medical imaging projection data in the matrix with the at least two sets of medical imaging projection data and reconstructing an image of the subject acquired while undergoing motion using the estimated medical imaging projection data and the at least two sets of medical imaging projection data stored in the matrix.

21. The method of claim 18 wherein estimating the medical imaging projection data includes combining consecutive partial scans with a selected weighting factor in a temporal domain.

* * * * *